| United States Patent [19] | [11] Patent Number: 4,816,413 |
|---|---|
| Sinor et al. | [45] Date of Patent: Mar. 28, 1989 |

[54] SOLID PHASE INDICATOR RED BLOOD CELLS AND METHOD

[75] Inventors: Lyle T. Sinor, Merriam; Frederick V. Plapp, Overland Park, both of Kans.; Jane M. Rachel, Kansas City, Mo.

[73] Assignee: Immucor, Inc., Norcross, Ga.

[21] Appl. No.: 904,948

[22] Filed: Sep. 8, 1986

[51] Int. Cl.$^4$ .................. G01N 33/555; G01N 33/549
[52] U.S. Cl. ......................................... 436/520; 435/7; 436/501; 436/512; 436/513; 436/521; 436/529; 436/532; 436/538; 436/824
[58] Field of Search ..................... 435/7, 180; 436/501, 436/512, 513, 521, 529, 532, 538, 520, 824

[56] References Cited

U.S. PATENT DOCUMENTS

| | | | |
|---|---|---|---|
| 4,326,027 | 4/1982 | Wenz | 424/11 X |
| 4,403,037 | 9/1983 | Coates | 436/521 |
| 4,587,222 | 6/1986 | Gaffroy | 436/521 X |
| 4,608,246 | 8/1986 | Bayer et al. | 436/520 X |

*Primary Examiner*—Robert J. Warden
*Assistant Examiner*—Richard Wagner
*Attorney, Agent, or Firm*—Kokjer, Kircher, Bradley, Wharton, Bowman & Johnson

[57] ABSTRACT

A method and composition for use in preparing red blood cells for use as indicator cells to detect the presence of antigens and antibodies in biological fluids is the subject of the present invention. Freshly collected human or animal erythrocytes are washed six times with isotonic saline, and suspended to a hematocrit of four percent (volume/volume) with isotonic saline. An incomplete antibody, specific for the antigen or antibody to be detected, in a quantity less than that which would cause irreversible agglutination, is added to the erythrocyte solution. The mixture is incubated, washed, and suspended to a hematocrit of 3-5 (v/v) with isotonic saline. A second antibody, immuno specific for the first antibody and in an amount sufficiently great to immunologically bind substantially all of the antibody carrying red blood cells but not so great as to cause irreversible agglutination, is attached to the erythrocytes. This mixture is incubated, washed, and suspended to a hematocrit of 0.1-1% (v/v) in a media containing red blood cell nutrients. The resulting indicator red blood cells are used with solid phase immunological testing using various types of solid substrates.

13 Claims, No Drawings

SOLID PHASE INDICATOR RED BLOOD CELLS AND METHOD

BACKGROUND

This invention relates generally to the field of immunological reactions in biological fluids and, more particularly, to a method and comparison useful in preparing red blood cells for use as indicator cells to detect the presence of antigens and antibodies in biological fluids.

The traditional method of determining ABO and Rh grouping, antibody screening, antibody identification and cross-matching is biological fluids such as blood, serum, and saliva, is through agglutination reactions. Until relatively recently, agglutination tests have been limited by their need to be performed manually. One of the primary reasons for requiring manual observation is the lack of an easily discernible end point. Various reagents are now available to increase the sensitivity and reliability of agglutination reactions to permit at least semi-automation. Even with the improved techniques, agglutination reactions still face the drawback of lacking an objective end point. Sophisticated electronic equipment partially compensates for this drawback, but such equipment is expensive and is not feasible for many smaller laboratories.

It has long been known that antibodies and antigens may be absorbed onto the surface of erythrocytes to detect the presence of immunoglobulins and anti-immunoglobulins in biological fluids utilizing passive agglutination reactions. The protein antigens and antibodies will not immunologically adhere to the erythrocytes unless the cell structure is altered or coupling agents are employed. Once suitable modification of the red cells is achieved and antigens of antibodies are then attached, it known to utilize the resulting indicator red blood cells to determine the presence of antigens and antibodies in biological fluids using passive agglutination reactions. These reactions have most frequently been carried out in liquid phase assays. Even when improved indicator red blood cells of the type described above are employed in liquid phase assays, some of the same problems associated with conventional agglutination reactions are encountered including lack of sensitivity and difficulty in determining end points. A technique for utilizing red blood cells as indicators of an immunological reaction in liquid phase assays is discussed in detail in the book "Immuno Assays for the 80s" by A. Voller et al., especially Chapter 3 by R. R. A. Coombs, published by University Park Press, Baltimore, Maryland, 1981. Even utilizing the improved techniques of Coombs and other pioneers in the field, employment of indicator red blood cells in liquid phase serology is still limited by the lack of a clearly discernible and objective end point.

A considerable advance in the art of blood group serology is represented by U.S. Pat. No. 4,275,053 to Rosenfield issued June 23, 1981. This patent is directed to a procedure for conducting blood group serology in solid phase. The disadvantage of liquid phase hemagglutination tests as well as the advantages of working in the solid phase are discussed in detail in the referenced patent. The single greatest advantage of solid phase assays is the use of immune adherence rather than hemagglutination for the detection of antigen-antibody reactions. This is a much more objective and discernible end point for either manual or automated reading.

A further advantage in solid phase assays for determining the presence of antibodies and antigens in biological fluids is described in U.S. Pat. No. 4,608,246 to Bayer, Plapp, Sinor et al., issued Aug. 26, 1986. In the Bayer, Plapp, Sinor et al. patent, a technique for broad application of solid phase blood group serology is described. The method disclosed offers numerous advantages over the original concept described in the Rosenfield patent including applicability to a broader range of substrates, fewer steps, longer shelf life, and a shorter time for carrying out the tests. A distinguishing characteristic of the Bayer, Plapp, Sinor et al. method is the utilization of proteolytic enzymes to activate the red blood cells prior to subjecting them to an immunological reaction.

When utilizing any of the prior art techniques for modifying red cell structures in order to bind antibodies and utilize the cells as indicator cells in liquid phase technology, the agent utilized to modify the cells tends to render the cells "sticky". When these indicator red blood cells are used in solid phase red cell adherence assays, this "stickiness" prevents a clear cut distinction between positive and negative results. Even utilizing enzyme activation as taught by Bayer, Plapp, Sinor, et al., preparation of the indicator cells is time consuming, requires large amounts of antibody, and the shelf life of indicator cells is relatively short. Also, the enzyme treatment as well as other activation techniques may destroy some antigens.

SUMMARY OF THE INVENTION

The present invention provides for indicator red blood cells to which specific antibodies have been attached without the use of fixing agents or enzyme pretreatment of the red blood cells.

Objects of the Invention

A primary objective of this invention is to provide indicator red blood cells for use in immunological reactions which are not "sticky" and, accordingly, are suitable for use in solid phase assays.

Another one of the objects of the invention is to provide indicator red blood cells wherein no modification of the cells or enzyme pretreatment is required in order to activate the cells for use as indicators.

A very important aim of the invention is to provide for indicator red blood cells which do not exhibit "stickiness" and, accordingly, are suitable for use in immunological reactions where the end point is detected by immunoadherence rather than hemagglutination.

One of the aims of our invention is to provide indicator red blood cells meeting the objects heretofore set forth which can be used with a variety of artificial substrates suitable for solid phase assays.

Still another one of the objects of the invention is to provide indicator red blood cells which have not been modified or pretreated with enzyme to achieve activation which can still maintain a relatively long shelf life.

Our invention also has as an aim to provide indicator red blood cells which can be activated for use in immunological reactions as end point indicators wherein none of the antigens on the indicator cells are destroyed during the activation process.

Another object of the invention is to provide indicator red blood cells which do not require cell modification or enzyme preactivation and which can be used with any incomplete antibody.

A corollary to the foregoing objects is to provide indicator red blood cells meeting the aims and objectives set forth which can be used with any biological fluid.

Other objects of the invention will be made clear or become apparent from the following description and claims.

DETAILED DESCRIPTION OF THE INVENTION

The erythrocytes employed to provide the indicator red blood cells according to the present invention may be human or from animal sources, for example bovine or murine. The freshly collected red blood cells are washed six times with isotonic saline to remove other components which may be present in the blood. After the last wash, the red blood cells are suspended to a hematocrit of 3-5 percent (volume/volume) with isotonic saline.

To sensitize the erythrocytes for use as indicator cells, any non-agglutinating or incomplete antibody may be used. These include the classes IgG, IgA, IgD and IgE. Some species of the class IgM may be incomplete and therefore acceptable. The selection of the particular antibody will depend upon the antigen or antibody to be detected using a particular indicator cell.

It is important that the quantity of antibody utilized to sensitize the erythrocytes be sufficient to impart immunological activity to the cells without effecting irreverisble agglutination. To maximize the sensitivity of the indicator cells the quantity of antibody attached should be sufficient to immunologically bind substantially all of the available antigenic sites on the cells. The actual quantitative requirments for a particular sensitizing antibody will generally be determined empirically. This can be done by adding antibody until irreversible agglutination occurs and then reducing the titer from this level until a positive reaction is no longer attainable. An acceptable titer is between these two extremes. The titer of the sensitizing antibody, for most species, will come within the range of from 1:10 to 1:512 (antibody:-buffer).

Once the antibody is added to the erythrocyte solution, the mixture is incubated from 5 to 60 minutes at 20°-37° C. to allow the antibodies to immunologically bind to the red blood cells. After the incubation period, the cells are again washed six times in isotonic saline to remove any unbound components. The washed cells are then suspended to a hematocrit of 4% (v/v) with isotonic saline.

Next, a second antibody that is immuno specific for the first antibody attached to the erythrocytes is attached to the antibody-carrying red blood cells. For example, if IgG antibodies have been attached to the cells according to the procedure outlined above, anti-IgG is attached as a second step in preparing the erytrocytes for use as indicator red blood cells. At this stage, it is desirable that a sufficient quantity of anti-immunoglobulin be added so as to immunologically bind substantially all of the antibody-carrying red blood cells. While lesser quantities can be employed, this will detract from the ultimate sensitivity of the indicator cells. In no case should the quantity of anti-immunoglobulin be high enough to irreversibly agglutinate the sensitized red blood cells. The actual quantitative requirements for a particular anti-immunoglobulin will generally be determined empirically in the same manner described for the sensitizing antibody. The titer of the anti-immunoglobulin, for most species, will come within the range of from 1:10 to 1:128 (anti-immunoglobulin:buffer).

Once the anti-immunoglobulin is added to the erythrocyte solution, the mixture is incubated from 5 to 60 minutes at 20°-37° C. to allow the anti-immunoglobulin to bind to the antibody previously bound to the red blood cells. After the incubation period, the cells are washed six times with isotonic saline to remove any unbound components. The finished indicator cells are then suspended to a hematocrit of 0.1-1% (v/v) in a media containing red blood cell nutrients. Appropriate nutrient/preservative solutions are well known to those skilled in the art. Since the suspended red blood cells are undergoing glycolysis, the media should contain glucose and adenosine. The shelf life of the product is extended if glycolysis is slowed and yeast and bacterial growth are prevented. This may be done by storing at a temperture of approximately 4° C.

It is to be understood that, while the invention has been explained in terms of a single antibody being attached to the erythrocyte to present an indicator red blood cell, groups of antibodies may also be immunologically bound where broader screening is desired. In this case, anti-immunoglobulin that is polyspecific for the sensitizing antibodies previously attached to the erythrocytes are used in the second step.

The primary utility of the indicator red blood cells prepared according to the present invention is for use with solid phase immunological testing. Various types of solid substrates for carrying out solid phase reactions are now well known to those skilled in the art. Suitable materials include polystyrene, polyvinyl, nylon, and nitro cellulose membranes. In the preferred embodiment of the invention, the substrate is a microplate having wells or recesses for receipt of the sample and deposit of the indicator cells. The general procedure is to attach antigens or antibodies to the solid surface using techniques which are now well known to those skilled in the art. The solid surface is then washed to remove any unbound antigens or antibodies and the unknown sample being tested is added. After incubation, unbound antigens or antibodies are removed by washing, and the indicator red blood cells are added. If antigens or antibodies specific for the antibody which is attached to the indicator cell is present, a positive reaction will occur binding the indicator red blood cells to the solid phase support. If microplates are used, they should be centrifuged after which the indicator red blood cells remain bound to the solid surface and efface the general area covered by the immobilized antigen or antibody from the unknown sample. With some substrates, simple washing may be utilized in place of centrifugation. In the event that the antibody or antigen specific for the antibody attached to the indicator cells is absent in the unknown sample, the indicator cells will not bind to the solid surface since there is nothing to effect immunoadherence of the indicator cells. Upon centrifugation, washing, or both, the indicator red blood cells will be washed from the surface or will collapse into a pellet at the bottom of a microplate well. This provides a clear indication of a negative reaction.

EXAMPLE 1

Red Blood Cell Antibody Screening and Identification

This assay is designed to detect antibodies found in donor or patient fluid specific for antigens on the surface of red blood cells. Therefore, the solid phase consists of an immobilized red-cell monolayer of known antigenic composition. The assay is performed within microplates by adding a drop of serum or plasma to the red-cell-coated microplate wells. The serum plasma may be diluted ½ to ¼ with a low ionic strength solution, such as 1.9% glycene, pH 7.0, to increase the rate of reaction of some antigens and antibodies. The microplate is incubated at 37° C. for 10 minutes and washed four times with saline. One drop of a 0.5% (v/v) suspension of indicator red blood cells is added to each microplate well, after which the microplates are centrifuged at 600 ×g for 1 minute. Positive reactions are characterized by effacement of the indicator red blood cells over the well cavities as described above. In negative reactions, the indicator red blood cells will be found, after centrifugation, as a small clump or button in the bottom of the well.

EXAMPLE 2

Platelet Antibody Screening and Identification

This test is substantially the same as the above test for red blood cell antigens, except that the solid phase consists of platelets immobilized onto the surface of the microplate. Positive and negative reactions are characterized in the same manner as indicated for Example 1.

EXAMPLE 3

Leukocyte Antibody Screening and Identification

This test is substantially the same as the tests of Examples 1 and 2 except that the solid phase consists of leukocytes immobilized onto the surface of the microplate. Various classifications of leukocytes (e.g. T-helper lymphocytes, T-suppressor lymphocytes, natural killer cells, and granulocytes) may be used in the assay. Positive and negative reactions are characterized in a manner indicated for Example 1.

EXAMPLE 4

Detection of Antibodies Specific for HBsAg

In this assay, HBsAg virus particles, or purified HBsAg antigens, are immobilized on the surface of the microplate. Otherwise the procedure is the same as given in Example 1. Donor or patient serum is added to the microplate well. If the sample contains antibodies specific for HBsAg antigens, they bind immunologically to the immobilized HBsAg. Other molecules are washed away. To detect the anti-HBsAg antibodies, the indicator red blood cells are added and positive and negative reactions are characterized in the manner indicated in Example 1.

EXAMPLE 5

Detection of Antibodies specific for HTLV-III

This assay is designed to detect antibodies to the HTLV-III virus in patient or donor serum. The procedure set forth in Example 1 is followed except that HTLV-III virus particles, or purified components of the HTLV-III virus are immobilized onto the surface of microplate wells. Donor or patient serum is added to the microplate wells. If antibodies specific for HTLV-III are present, they bind immunologically to the immobilized HTLV-III antigens. Other molecules are washed away. The indicator red blood cells are added and positive and negative reactions are characterized as set forth in Example 1.

EXAMPLE 6

Detection of Antibodies Specific for Cytomegalovirus (CMV)

This test is very similar to the HTLV-III test set forth in Example 5. The only difference is that CMV virus or purified virus antigens are immobilized upon the microplate wells. Donor or patient serum is added to the microplate wells. If anti-CMV antibodies are present, they bind immunologically to the immobilized CMV virus antigens. Following washing to remove unbound components of the serum, the indicator red blood cells are added. Positive and negative reactions are characterized as indicated in the previous examples.

All of the examples cited above utilize a microplate as the solid phase support. All of the above tests can be performed upon alternative solid phase supports, including nitrocellolose, nylon, or positively charged nylon.

We claim:

1. A method of preparing indicator red blood cells for detecting the presence of antigens and antibodies in biological fluids, said method comprising the steps of:
    providing a supply of red blood cells;
    sensitizing said red blood cells by contacting same with a known non-agglutinating antibody in a quantity sufficient to immunologically react with substantially all of the antigenic sites on said red blood cells thereby causing immunological adherence of the red cells and the antibody, said quantity being insufficient to effect irreversible agglutination of said cells;
    adding to said sensitized red blood cells a sufficient quantity of anti-immunoglobulin having immunogenicity for said antibody whereby said anti-immunoglobulin will immunologically adhere to said antibody, said quantity being insufficient to effect irreversible agglutination of said cell;
    whereby said added anti-immunoglobulin remains available for immunological binding with an immunological counterpart present in an unknown sample.

2. A method as set forth in claim 1, wherein said sensitizing step includes incubating the mixture of red blood cells and antibody for a sufficient period of time for said immunological adherence to occur.

3. A method as set forth in claim 2, wherein said adding step comprises incubating the mixture of sensitized red blood cells and anti-immunoglobulin for a period of time sufficient for said immunological adherence to occur.

4. A method as set forth in claim 3, wherein said adding step comprises adding a sufficient quantity of said anti-immunoglobulin to immunologically react with substantially all of the antibodies that are immunologically adhered to said red blood cells.

5. A method as set forth in claim 4, wherein said adding step comprises adding a quantity of said anti-immunoglobulin equal to the quantity of said antibody utilizes in said sensitizing step.

6. A method as set forth in claim 1, wherein said sensitizing step comprises contacting said red blood cells with at least two known antibodies and said adding step comprises adding immunoglobulin having immunogenicity for all of said antibodies.

7. A method of preparing indicator red blood cells for detecting the presence of antigens and antibodies in biological fluids, said method comprising the steps of:

providing a solution of red blood cells;

adding to said solution a solution of a known non-agglutinating antibody in a quantity sufficient to immunologically react with substantially all of the antigenic sites on said red blood cells, said quantity being insufficient to effect irreversible agglutination of said cells;

incubating the mixture of red blood cells and incomplete antibody at 20°-37° C. for a period of time sufficient to effect immunoadherence of the antibody and the red blood cells;

adding to said solution of red blood cells a solution of anti-immunoglobulin characterized by immunogenicity for said known antibody in a quantity sufficient to immunologically react with substantially all of the antibody carrying red blood cells, said quantity being insufficient to effect irreversible agglutination of said cells; and incubating the mixture of red blood cells and anti-immunoglobulin at 20°-37° C. for a period of time sufficient to effect immunoadherence of the anti-immunoglobulin and the antibody carrying red blood cells, whereby said added anti-immunoglobulin remains available for immunological binding with an immunological counterpart present in an unknown sample.

8. A method as set forth in claim 7, wherein is included after each of said incubating steps the step of washing said red blood cells in saline solution to remove any nonadhered antibody and anti-immunoglobulin.

9. A method as set forth in claim 10, wherein is included the final step of suspending said red blood cells to a hematocrit of 0.1 to 1% (v/v) in saline solution.

10. An indicator solution for use in determining the presence of antibodies and antigens in biological fluids, said indicator solution comprising:

a solution of red blood cells having an non-agglutinating antibody immunologically adhered thereto in a quantity sufficient to impart antigen binding activity to said red blood cells but insufficient to cause irreversible agglutination of said cells and anti-immunoglobulin immunologically ahdered to said antibody in a quantity sufficient to impart antibody binding activity to said red blood cells but insufficient to cause irreversible agglutination of said cells.

11. An indicator solution as set forth in claim 10, wherein said solution comprises saline and said red blood cells are present at a concentration of about 0.1 to 1% volume/volume.

12. An indicator solution as set forth in claim 10, wherein at least two different known antibodies are immunologically adhered to said red blood cells and anti-immunoglobulin having immunogenicity for said different antibodies is immunologically adhered to said antibodies.

13. An indicator solution as set forth in claim 10 wherein is included glucose and adenosine.

* * * * *